United States Patent [19]

Ozawa et al.

[11] Patent Number: 4,743,274
[45] Date of Patent: May 10, 1988

[54] ORAL COMPOSITION AND ABRASIVE THEREFOR

[75] Inventors: Toshiyuki Ozawa, Chigasaki; Osamu Uotani, Chiba; Rieko Hayashi, Odawara, all of Japan

[73] Assignee: Lion Corporation, Tokyo, Japan

[21] Appl. No.: 824,198

[22] Filed: Jan. 30, 1986

Related U.S. Application Data

[62] Division of Ser. No. 566,681, Dec. 29, 1983, Pat. No. 4,587,120.

[30] Foreign Application Priority Data

Dec. 29, 1982 [JP] Japan ................................ 57-228601
Dec. 29, 1982 [JP] Japan ................................ 57-228602

[51] Int. Cl.$^4$ ............................................. B24D 3/02
[52] U.S. Cl. ........................................ 51/309; 424/57
[58] Field of Search ............................ 424/57; 51/309

[56] References Cited

U.S. PATENT DOCUMENTS

| | | | |
|---|---|---|---|
| 2,018,410 | 10/1935 | McDonald et al. .................. | 167/93 |
| 3,012,852 | 12/1961 | Nelson .................................. | 424/57 |
| 3,066,056 | 11/1962 | Schlaeger et al. .................... | 424/57 |
| 3,169,096 | 2/1965 | Schlaeger et al. .................... | 424/57 |
| 3,647,371 | 3/1972 | Kim et al. ............................. | 424/57 |
| 3,829,562 | 8/1974 | Kim et al. ............................. | 424/57 |
| 4,038,380 | 7/1977 | Cordon ................................. | 51/309 |
| 4,108,961 | 8/1978 | Ploger et al. ......................... | 424/57 |
| 4,108,962 | 8/1978 | Ploger et al. ......................... | 424/57 |
| 4,130,630 | 12/1978 | Ploger et al. ......................... | 424/57 |
| 4,244,707 | 1/1981 | Wason .................................. | 51/309 |
| 4,280,822 | 7/1981 | Wason .................................. | 51/309 |
| 4,444,570 | 4/1984 | Barth et al. .......................... | 51/309 |
| 4,587,120 | 5/1986 | Ozawa et al. ........................ | 424/57 |

FOREIGN PATENT DOCUMENTS 47-2431 1/1972 Japan .
53-124631 10/1978 Japan .

*Primary Examiner*—A. Lionel Clingman
*Assistant Examiner*—Willie J. Thompson
*Attorney, Agent, or Firm*—Birch, Stewart, Kolasch & Birch

[57] ABSTRACT

Calcium hydrogenphosphate anhydride is disclosed whose crystallite has an average size of 300 to 3,500 angstroms as measured by X-ray diffractometry, and preferably, which has a density of 2.650 to 2.885 grams per cubic centimeters, a specific surface area of 2.5 to 20 square meters per gram as measured by the BET method, and an average agglomerate diameter of 2 to 30 micronmeters has good physical properties as an abrasive, and that when it is used as an abrasive in an oral composition, the resulting oral composition is improved in cleaning action and in the effect of making the tooth aesthetically white without increasing its abrasiveness.

12 Claims, 3 Drawing Sheets

ORAL COMPOSITION AND ABRASIVE THEREFOR

This application is a division of application Ser. No. 566,681, filed Dec. 29, 1983, now U.S. Pat. No. 4,587,120.

BACKGROUND OF THE INVENTION

This invention relates to an abrasive for use in oral compositions such as dentrifrices, prophylactic pastes and the like. More particularly, this invention relates to a highly cleaning, low abrading abrasive for use in oral compositions which consists of calcium hydrogenphosphate anhydride (secondary calcium phosphate anhydride) whose crystallite has an average size of 300 to 3,500 angstroms as measured by X-ray diffractometry. This invention also relates to an oral composition containing the abrasive.

In general, abrasives for use in oral compositions, for example, dentifrices and prophylactic pastes are required to have an increased ability of efficiently removing away stain, dental plaque, and food debris adhered to or deposited on teeth with the aid of physical action, that is, an improved cleanability as a tooth cleaning agent, and to exhibit mild abrasiveness to such an extent that the tooth enamel will not be damaged, as well as to prevent deposition of dental plaque and calculus.

In this case, the efficiency of physical removal of stain, plaque, and food debris can be increased by using an abrasive having increased abrasiveness. Particularly, it has been a common practice in the prior art to enhance the cleaning effect of an abrasive on the tooth surface by increasing the abrasiveness thereof. However, increasing abrasiveness is generally opposite to the prevention of damage to the tooth surface. The higher the abrasiveness, the greater is the likelihood that the tooth surface would be abraded away. Particularly when brushing is done inadequately, there is the increased likelihood that wedge-shaped deffects would be formed and the tooth surface would be marred or scratched and reduced in luster. Thus, there is a need for an abrasive for use in oral compositions which will not cause damage to the tooth surface while retaining a proper degree of abrasiveness and having improved cleaning effect.

SUMMARY OF THE INVENTION

It is, therefore, an object of the present invention to provide an abrasive for use in oral compositions in which cleaning action is improved without increasing abrading action.

It is another object of the invention to provide an oral composition comprising an abrasive having an improved cleaning action without increasing abrading action.

As a result of extensive investigations to meet the above-mentioned need, the inventors have found that calcium hydrogenphosphate anhydride (secondary calcium phosphate anhydride) whose crystallite has an average size of 300 to 3,500 angstroms as measured by X-ray diffractometry, and preferably, which has a density of 2.650 to 2.885 grams per cubic centimeters, a specific surface area of 2.5 to 20 square meters per gram as measured by the BET (Brunauer-Emmett-Teller) method, and an average agglomerate diameter of 2 to 30 micronmeters has good physical properties as an abrasive, and that when the above-defined calcium hydrogenphosphate anhydride is used as an abrasive in an oral composition, the resulting oral composition is improved in cleaning action and in the effect of making the tooth aesthetically white without increasing its abrasiveness.

It was difficult in the prior art to enhance the cleaning action and to lower the abrading action of an abrasive at the same time inasmuch as the cleaning action of conventional abrasives is substantially proportional to the abrading action thereof, and it is thus imperative for cleaning enhancement to increase abrading action. On the contrary to such conventional belief, the inventors have found that calcium hydrogenphosphate anhydride having crystallites of a size having an average value of 300 to 3,500 angstroms as measured by X-ray diffractometry exhibits improved cleaning action irrespective of its low abrasiveness as demonstrated in experiments to be described later, and thus, the use of this calcium hydrogenphosphate anhydride alone is sufficiently effective to clean up the tooth without impairing the dental enamel, meeting both the requirements of high cleanability and low abrasiveness at the same time with the additional benefit of making the tooth aesthetically white.

It is well known in the art to use calcium hydrogenphosphate anhydride (secondary calcium phosphate anhydride) as an abrasive for dentifrices or the like. However, such previously used calcium hydrogenphosphate anhydride usually has an average crystallite size of 3,800 to 4,300 angstroms as measured by X-ray diffractometry, a specific surface area of about 1 to 2 $m^2/g$ as measured by the BET method, and a density of 2.890 $g/cm^3$ and has a microscopic-structure (a particle shape) as shown in FIG. 1, and as a result, exhibits too high abrasiveness as shown in experiments to be described later as long as it is in the form of single particle having a normal particle size, that is, a particle diameter of 10 to 30 microns. When such conventional calcium hydrogenphosphate anhydride is used alone as an abrasive, the resulting oral composition will show an abrasiveness value of above 250, as measured by the RDA (Radio Active Dentin Abrasion) method, which value is generally regarded as the upper limit by the ADA (American Dental Association) and other dental associations, and thus has the possibility of inducing wedge-shaped defects after long term repeated use if the brushing way is inadequate. For this reason, the conventional calcium hydrogenphosphate anhydride abrasive was used in combination with other mild abrasives. As compared with the conventional ones, the calcium hydrogenphosphate anhydride (secondary calcium phosphate anhydride) of the present invention has an average crystallite size of 300 to 3,500 angstroms as measured by X-ray diffractometry, has less sharp edges or more round edges, exhibits extremely low abrading action so that it can be used as a sole abrasive, and exhibits more cleaning action (or stain removing action) than other types of abrasive having a similar degree of abrasiveness, with the additional benefit of making the tooth aesthetically white. These are new findings made by the inventors.

BRIEF EXPLANATION OF THE DRAWINGS

FIGS. 7 to 10 are diagramatic illustrations of the abrasiveness vs. the cleanability of various calcium hydrogenphosphate samples, respectively.

DETAILED DESCRIPTION OF THE INVENTION

The abrasive for use in oral compositions according to the present invention consists of calcium hydrogenphosphate anhydride (secondary calcium phosphate anhydride) whose crystallite has an average size (also referred to as "average crystallite size" herein) of 300 to 3,500 angstroms as measured by X-ray diffractometry as will be demonstrated in the experiment shown below, and which has a microscopic structure as shown in FIGS. 2-5. Because of its crystalline attributes, the calcium hydrogenphosphate anhydride of the invention exhibits a moderate degree of abrasiveness and a high degree of cleaning to the tooth, and at the same time, is effective for making the tooth aesthetically white.

The calcium hydrogenphosphate anhydride which is useful in the present invention has an average crystallite size of 300 to 3,500 angstroms, with one having an average crystallite size of 300 to 3,000 angstroms being particularly preferred for improved cleaning action. If the average crystallite size is less than 300 angstroms, the phosphate shows too low cleaning action, and if the average crystallite size is more than 3,500 angstroms, the phosphate shows too high abrasiveness, both failing to achieve the objects of the invention.

Preferably, the calcium hydrogenphosphate anhydride useful in the present invention has a density of 2.650 to 2.885 g/cm$^3$, more preferably 2.750 to 2.885 g/cm$^3$ at 20° C., a specific surface area of 2.5 to 20 m$^2$/g, more preferably 3 to 10 m$^2$/g as measured by the BET method, and an average agglomerate diameter of 2 to 30 microns, more preferably 5 to 25 microns as measured by the laser light-scattering photometry, and has a microscope structure as shown in FIGS. 2 to 5.

Figure 1:
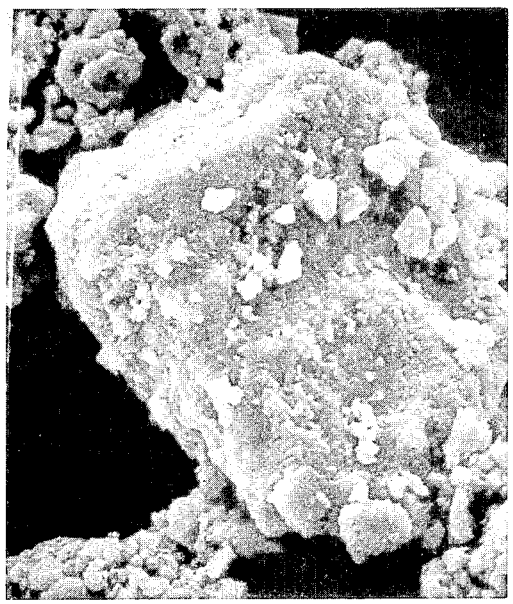
FIG. 1 is a photomicrograph (3000× magnification) of a prior art calcium hydrogenphosphate anhydride sample.

The conventional prior art calcium hydrogenphosphate anhydride has an average crystallite size of 3,800 to 4,300 angstroms, a density of 2.890 g/cm$^3$ at 20° C., a specific surface area of about 1 to 2 m$^2$/g as measured by the BET method, and a microscopic structure as shown in FIG. 1, and thus exhibits too high abrasiveness as shown in experiments to be described later as long as it is in the form of single particle having a normal particle diameter of 10 to 30 microns. When such conventional one is used alone as a sole abrasive, the resulting oral composition will show an abrasiveness value of above 250 as measured by the RDA method and thus may induce wedge-shaped defects after long term repeated use if the brushing way is inadequate. On the other hand, the calcium hydrogenphosphate anhydride of the present invention having an average crystallite size, a density, specific surface area and average agglomerate size within the above-defined ranges exhibits extremely reduced abrading action as compared with the conventional ones so that it can be used alone as a sole abrasive for oral compositions, and at the same time, exhibits more cleaning action or stain removing action than other types of abrasive having a similar degree of abrasiveness and is very effective for making the tooth aesthetically white. It should be noted that the calcium hydrogenphosphate anhydride of the invention tends to increase its specific surface area and reduce its density as its average crystallite size is reduced.

The term "density" used herein is a measurement using a pycnometer followed by calculation according to the following formula:

$$\rho_P = \frac{M_S - M_O}{(M_L - M_O) - (M_{SL} - M_S)} \cdot \rho_L$$

where
  $M_S$: the weight of the pycnometer plus the weight of a powder sample,
  $M_O$: the weight of the pycnometer,
  $M_L$: the weight of the pycnometer filled with liquid (water),
  $M_{SL}$: the weight of the pycnometer filled with a powder sample and further with liquid (water), that is, [pycnometer weight + powder weight + liquid weight],
  $\rho_L$: the density of the liquid (water) at 20° C., and
  $\rho_P$: the density of the powder at 20° C.

Figure 2:
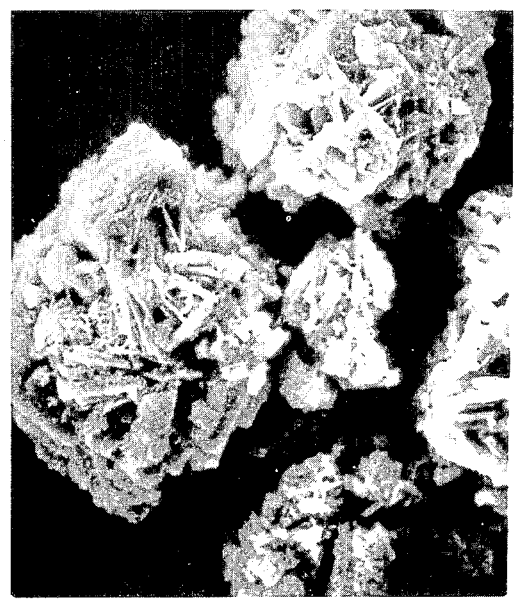
FIGS. 2 to 5 are photomicrographs of calcium hydrogenphosphate anhydride samples of the present invention, each of the photomicrographs of FIGS. 2 to 4 having a magnification of 3000 and the photomicrographs of FIG. 5 having a magnification of 2000, FIG. 6 schematically illustrates a spherulitic calcium hydrogenphosphate anhydride crystal according to the present invention.
Figure 3:
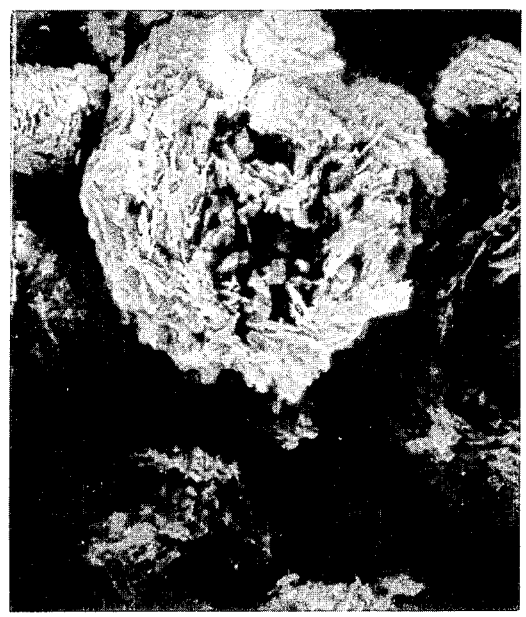
Figure 4:
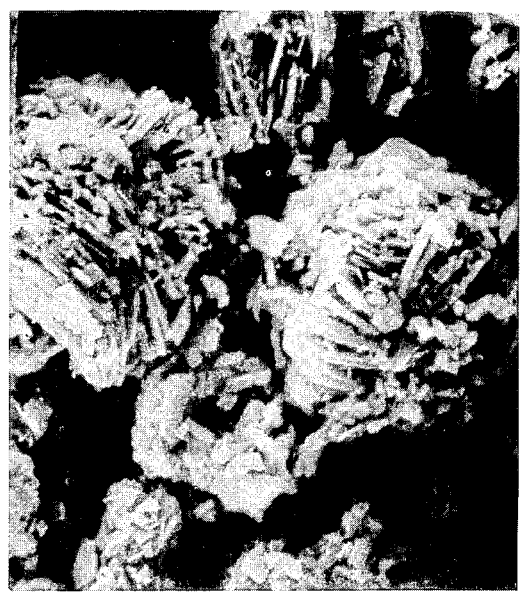

The calcium hydrogenphosphate anhydride useful herein is preferably in the form of a cohesive aggregate of plate crystals whose primary particle has an average particle size of 0.1 to 5 microns and which has a microscopic structure as shown in FIGS. 2-4. This is preferred for the following reason. In general, oral compositions, for example, dentifrices are preferably required to have improved juice effect, little change the taste of food, and give a pleasant feel to the mouth. To this end, for instance, it has been proposed to add N-alkyloylsarcosinates such as sodium N-lauroylsarcosinate to oral compositions to enhance the juice effect, or to substitute α-olefin sulfonates for alkyl sulfates. However, the addition of N-alkyloylsarcosinates has some problems, for example, the amount of the compound added is restricted to 0.5% by weight or less in view of mucous membrane separation. There is a need for an abrasive which when incorporated in oral compositions, can increase the juice effect and improve the mouth feel. It has been found that the calcium hydrogenphosphate anhydride of the present invention in the form of cohesive aggregate of plate crystals whose primary particle has an average particle size of 0.1 to 5 microns can, when used as such an abrasive for oral compositions, increase the cleaning action of the compositions without increasing the abrading action, so that an improved oral composition is obtained which causes little scratch to the dental enamel and has excellent juice effect and a pleasant feel to the mouth. The average value of the size of primary particles is obtained from a measurement on an electron micrograph followed by calculation. The above-defined calcium hydrogenphosphate anhydride has a microscopic structure as shown in FIGS. 2 to 4, that is, a structure in which plate or flake crystals aggregate or closely stack one on top of another like a pine cone to form a cohesive body with or without microfine particles of indefinite crystalline structure.

Figure 5:
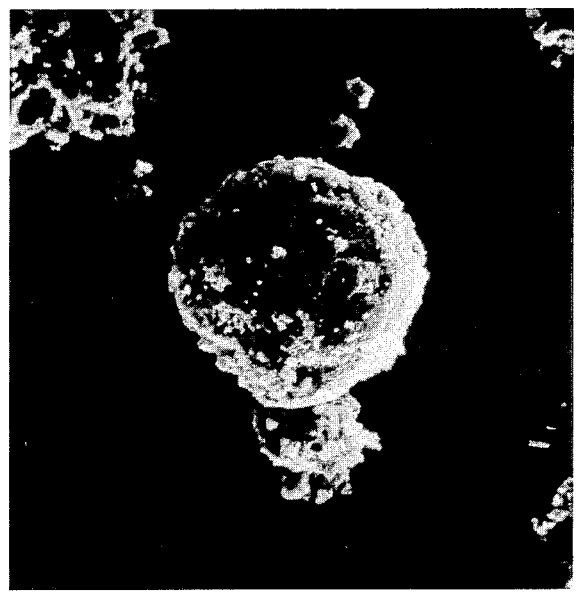

The calcium hydrogenphosphate anhydride useful in the present invention may also include a spherulitic calcium hydrogenphosphate anhydride as shown in FIG. 5. This spherulitic calcium hydrogenphosphate anhydride is comparable in cleaning action to conventional abrasives having an arbrasivity on copper plate of about 20 to 30 mg when it has an abrasivity on copper plate of about 1 to 5 mg, and to other conventional abrasives having the abrasivity of about 30 to 50 mg when it has the abrasivity of about 5 to 20 mg, as will be seen in experiments to be described later. In addition to such a unique combination of low abrasiveness with high cleanability, the spherulitic calcium hydrogenphosphate anhydride has an improved lustering effect so that sufficient luster is imparted to the tooth surface even when it is used alone as an abrasive. As compared with oral compositions containing a conventional subangular calcium hydrogenphosphate anhydride abrasive consistig of a mixture of plate, prism and needle crystals, oral compositions containing this spherulitic calcium hydrogenphosphate anhydride give little gritty feel to the oral cavity, is mild to the oral membrane, and thus give a pleasant feel to the mouth. Namely, the use of spherulitic calcium hydrogenphosphate anhydride can meet the requirements of high cleanability, low abrasiveness, high lustering, and pleasant feel at the same time. The conventional prior art calcium hydrogenphosphate anhydride having an average agglomerate size of 10 to 30 microns is of a subangular shape as shown in FIG. 1 and has a roundness of about 0.4 and a specific surface area of about 1 to 2 m$^2$/g as measured by the BET method, and thus exhibits too high abrading action as shown in experiments to be described later as long as it is in the form of agglomerates having a normal particle size. When such conventional one is used alone as a sole abrasive, the resulting oral composition will show an abrasion value of about 250 as measured by the RDA method and thus may induce wedge-shaped defects after long term repeated use, as described above. On the other hand, the spherulitic calcium hyrogenphosphate anhydride of the present invention exhibits increased cleaning action irrespective of reduced abrasiveness and is effective for imparting luster to the tooth surface at the same time.

Figure 6:
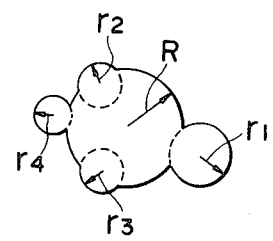

The spherulitic calcium hydrogenphosphate anhydride used herein preferably has an average roundness of 0.45 to 0.95, more preferably 0.5 to 0.9. The roundness is obtained from a photomicrograph and given by $$\frac{r_1 + r_2 + r_3 + \ldots + r_n}{RN}$$

where R is the radius of the maximum inscribed circle, $r_n$ is the radius of curvature of an n-th edge of a powder particle, and N is the number of measurements of r. One roundness measurement is shown in FIG. 6 in which an exemplary particle is illustrated with R, $r_1$, $r_2$, $r_3$, and $r_4$. The more round the shape, the more approximate to one the roundness is. For further information, reference should be made to Wadell, J., Geol., 40 (1932), 443-451. Also preferably, the spherulitic calcium hydrogenphosphate anhydride is one containing at least 70% of calcium hydrogenphosphate crystals as analyzed by X-ray diffractometry.

The calcium hydrogenphosphate anhydride of the present invention may be prepared in a conventional way, for example, by adding in the neutralizing reaction between phosphoric acid and lime milk a crysallization modifier capable of controlling the growth of crystals or effecting on crystal growth-kinetics, crystal habit and specific growth rates of individual crystal faces, as disclosed in U.S. Pat. Nos. 2,287,699 (1942), 3,012,852 (1961), 3,066,056 (1962), and 3,169,096 (1965), and Japanese Patent Publication Nos. 39-3272 and 39-3273 (1964). In this case, the crystallization modifiers used may preferably be phosphoric acid condensates and salts thereof, and be added in the course of neutralizing rection between phosphoric acid and lime milk. Also preferably, the amount of the crystallization modifier added ranges from 0.1 to 40% by weight, more preferably from 0.5 to 30% by weight based on the weight of the calcium hydrogenphosphate anhydride produced. As the amount of the modifier added increases, the growth of crystals is retarded and the size of crystallites becomes smaller. If the amount of the modifier added is less than 0.1% by weight, then crystallites will grow larger beyond the average size of 3,500 angstroms and result in increased abrasiveness. If the amount of the modifier added is more than 40% by weight, then crystallites will become smaller below the average size of 300 angstroms and will not exhibit low abrasion and high cleaning performance. The calcium hydrogenphosphate anhydride of the present invention may be prepared in a variety of grades by properly controlling the amount of the crystallization modifier added, the point and rate of addition of the modifier, phosphoric acid concentration, reaction temperature, reaction time, agitation speed and other parameters in the preparation procedure.

For instance, the calcium hydrogenphosphate anhydride of the present invention may preferably be prepared by reacting a calcium compound having an an electrolyte admixed therewith and a phosphoric acid compound at a temperature of 50° to 90° C. while adding a condensated phosphate to the reaction mixture.

The abrasive of the present invention may find uses in oral compositions including dentifrices such as toothpastes and powder dentifrices, and prophylactic pastes.

In these applications, the oral compositions having the abrasive of the present invention blended therein may contain any desired other ingredients depending on the type of the compositions and the like.

In the case of a dentifice composition, for example, the calcium hydrogenphosphate anhydride (secondary calcium phosphate anhydride) abrasive of the present invention may be used alone or in admixture with any other conventional abrasives, for example, calcium hydrogenphosphate dihydrate, conventional calcium hydrogenphosphate anhydride having an average crystallite size of 3,800 to 4,300 angstroms (falling outside the scope of the invention), calcium carbonate, calcium pyrophosphate, insoluble sodium metaphosphate, amorphous silica, crystalline silica, precipitated silica, aluminosilicate, aluminum oxide, aluminum hydroxide, microcrystalline cellulose, resin, magnesium tertiary phosphate, magnesium carbonate, etc. and mixtures thereof. When the calcium hydrogenphosphate anhydride of the present invention is combined with another abrasive or abrasives, the amount of the present phosphate used may preferably range from 5 to 100% by weight, more preferably from 10 to 100% by weight of the combined abrasives for taking the substantial advantage of the present phosphate.

In preparing oral compositions using the abrasive of the present invention, there may be blended any conventional ingredients, for example, binders such as sodium carboxymethyl cellulose, hydroxyethyl cellulose, alginates, carrageenan, gum arabic, polyvinyl alcohol, etc.; humectants such as polyethylene glycol, sorbitol, glycerin, propylene glycol, etc.; foaming agents such as sodium lauryl sulfate, sodium dodecylbenzenensulfonate, sodium hydrogenated coconut fatty acid monoglyceride monosulfate, sodium lauryl sulfoacetate, sodium N-lauroylsarcosinate, N-acylglutamates, lauroyl diethanolamide, sucrose fatty acid esters, etc.; flavoring agents, for example, essential oils such as peppermint oil, spearmint oil, etc. and flavors such as l-menthol, carvone, eugenol, anethol, etc.; sweeteners such as sodium saccharin, stevioside, neohesperidyl dihydrochalcone, glycyrrhizin, perillartine, p-methoxycinnamic aldehyde, somatine, etc.; preservatives; and pharmaceutical agents such as lysozyme chloride, dextranase, bacteriolytic enzymes, mutanase, chlorohesidine and salts thereof, sorbic acid, alexidine, hinokitiol, cetyl pyridinium chloride, alkyl glycines, alkyl diaminoethyl glycine salts, allantoin, ε-aminocaproic acid, tranexamic acid, azulene, vitamin E, sodium monofluorophosphate, sodium fluoride, stannous fluoride, water-soluble primary and secondary phosphoric acid salts, quaternary ammonium compounds, sodium chloride, etc. In preparing oral compositions using the abrasive of the present invention, magnesium tertiary phosphate is desirably blended therein to prevent pH lowering and hardening of the oral composition to thereby render the system more stable, preferably in an amount of 0.1 to 5% by weight, more preferably 0.5 to 3% by weight of the composition.

In an oral composition such as a dentifrice composition, the content of the abrasive may be in the range of 5 to 95% by weight, preferably 10 to 90% by weight of the composition. The content of the binder may be in the range of 0.1 to 5% by weight, preferably 0.3 to 3% by weight of the composition. The content of the humectant may be in the range of 1 to 70% by weight, preferably 10 to 60% by weight of the composition. The content of the foaming agent may be in the range of 0.1 to 10% by weight, preferably 0.2 to 5% by weight of the composition. The content of the flavor may be in the range of 0.1 to 5% by weight, preferably 0.3 to 2% by weight of the composition. The content of the sweetner may be in the range of 0.001 to 5% by weight, preferably 0.005 to 2% by weight of the composition.

The abrasive for use in oral compositions according to the present invention, which consists of calcium hydrogenphosphate anhydride whose crystallite has an average size of 300 to 3,500 angstroms as measured by X-ray diffractometry, exhibits a moderate degree of abrasion to the tooth as well as a high degree of cleaning action and is highly effective for making the tooth aesthetically white. Differently stated, since the calcium hydrogenphosphate anhydride having an average crystallite size within the above-defined range exhibits more cleaning action than other abrasives having the same degree of abrasion, it can clean off stain, plaque and food debris deposited to the tooth without damage to the tooth surface. The calcium hydrogenphosphate anhydride having an average crystallite size of 300 to 3,500 angstroms is significantly low in abrasiveness as compared with the conventional prior art calcium hydrogenphosphate anhydride having an average crystallite size of 3,800 to 4,300 angstroms, and thus it is not necessarily required to combine the former with other abrasives as required for the latter, that is, the former can be used alone as a sole abrasive for oral compositions.

An oral composition of the invention is prepared by blending the calcium hydrophosphate anhydride abrasive into an oral composition or mixing it with the other ingredients.

In order that those skilled in the art will more readily understand the invention, some exemplary procedures for preparing the calcium hydrogenphosphate anhydride of the invention will be presented below.

PREPARATION 1

Lime water is prepared by heating 3 liters of an aqueous solution having 4.0 grams of magnesium chloride dissolved therein to 80° C., pouring 380 grams of quick lime into the solution with stirring, and continuing stirring for 30 minutes to allow the quick lime to be slaked. The reaction mixture is passed through 100 mesh screen to remove coarse particles, obtaining lime water having a converted concentration of 124 grams of calcium oxide per liter.

Then, one liter of an aqueous solution of 75% phosphoric acid is heated to 75° C., and the above-prepared lime water is added to the solution at a rate of 600 milliliters/hour with stirring. At the point when the pH value of the reaction mixture has reached 2.2, pyrophosphoric acid having a $P_2O_5$ content of 80% is additionally added at a rate of 0.3 grams/minute concurrently with the addition of lime water. When the pH value has reached 2.8, the addition of pyrophosphoric acid is terminated. The addition of lime water is further continued until the pH value of the reaction solution reaches 5.0. The reaction solution is then filtered, and the filter cake is washed with water and dried at 60° C. for 24 hours. It was found that by varying the amount of a polyphosphoric acid or its salt, such as pyrophosphoric acid or sodium pyrophosphate added and controlling the starting point and rate of addition of a polyphosphoric acid or its salt, there can be obtained calcium hydrogenphosphate anhydride having correspondingly varying crystallite size, density and specific surface area.

PREPARATION 2

Lime water is prepared by heating 3 liters of an aqueous solution having 3.7 grams of magnesium chloride dissolved therein to 80° C., pouring 390 grams of quick lime into the solution with stirring, and continuing stirring for 30 minutes to allow the quick lime to be slaked. The reaction mixture is passed through the 100 mesh screen to remove coarse particles, obtaining lime water having a converted concentration of 128 grams of calcium oxide per liter.

Then, one liter of an aqueous solution of 75% phosphoric acid is heated to 78° C., and the above-prepared lime water is added to the solution at a rate of 570 milliliters/hour with stirring. At the point when the pH value of the reaction mixture has reached 0.8, pyrophosphoric acid is additionally added concurrently with the addition of lime water. When the pH value has reached 1.2, the addition of pyrophosphoric acid is terminated. The addition of lime water is further continued until the pH value of the reaction solution reaches 5. The total amount of lime water added is 5.3 liters, and the amount of pyrophosphoric acid added is 13.5 grams. This means that pyrophosphoric acid is added in an amount of 2.0 parts by weight per 100 parts by weight of calcium oxide. The reaction solution is then filtered, and the filter cake is washed with water and dried at 60° C. for 24 hours, obtaining calcium hydrogenphosphate anhydride within the scope of the present invention.

PREPARATION 3

Lime water is prepared by heating 3 liters of an aqueous solution having 3.4 grams of magnesium chloride dissolved therein to 80° C., pouring 393 grams of quick lime into the solution with stirring, and continuing stirring for 30 minutes to allow the quick lime to be slaked. The reaction mixture is passed through the 100 mesh screen to remove coarse particles, obtaining lime water having a converted concentration of 129 grams of calcium oxide per liter.

Then, one liter of an aqueous solution of 70% phosphoric acid is heated to 80° C., and the above-prepared lime water is added to the solution at a rate of 540 milliliters/hour with stirring. At the point when the pH value of the reaction mixture has reached 0.4, pyrophosphoric acid is additionally added concurrently with the addition of lime water. When the pH value of 1.0 is reached, the addition of pyrophosphoric acid is terminated. The addition of lime water is further continued until the pH value of the reaction solution reaches 5.0.

The total amount of lime water added is 5.2 liters, and the amount of pyrophosphoric acid added is 13.0 grams. This means that the pyrophosphoric acid is added in an amount of 1.94 parts by weight per 100 parts by weight of calcium oxide.

The product is filtered and dried in a conventional manner, obtaining calcium hydrogenphosphate anhydride falling within the scope of the present invention.

It was found that by controlling the starting point and rate of addition of pyrophosphoric acid, there can be obtained calcium hydrogenphosphate anhydride having varying degree of cleaning action.

PREPARATION 4

Lime water is prepared by heating 5 liters of water to 70° C., pouring about 650 grams of quick lime into the water, and continuing stirring for 30 minutes. The resulting lime water has a converted concentration of about 130 grams of calcium oxide per liter. Using the 100 mesh screen, coarse particles are removed from the lime water.

Then, one liter of an aqueous solution of 50% phosphoric acid having a pyrophosphate added thereto is heated to 73° C., and the above-prepared lime water is added to the solution at a rate of 1 liter/hour with stirring. At the end of reaction, the reaction solution is filtered, washed with water, and dried at 60° C. for about 24 hours, obtaining calcium hydrogenphosphate anhydride in spherulitic form.

It was found that by controlling the amount of the pyrophosphate added and other parameters, the roundness of the product can be controlled to the desired level.

Examples are presented below in order to illustrate the effects of the abrasive of the present invention.

EXAMPLE 1

A number of calcium hydrogenphosphate samples having different average crystallite sizes and average agglomerate diameters shown in Tables 1 and 2 were tested for abrasiveness and cleanability by the following methods, in order to examine the correlation between size and performance of abrasives. The calcium hydrogenphosphate anhydride samples used had a specific surface area of 2.5 to 20 m$^2$/g as measured by the BET method, and a density of 2.650 to 2.885 g/cm$^3$. The results are shown in Table 3.

The average crystallite size is measured by carrying out X-ray diffraction analysis on a powder sample. Based on the broadening of peaks, the crystallinity of the powder sample is quantitatively expressed using the size of crystallites as an index. Cu-K$\alpha$ ray is used for measurement as the X-ray source, and the data of X-ray diffraction are analyzed for non-overlapping predominant peaks using Scherrer's equation $D = K\lambda/\beta \cos \theta$, determining the average size of crystallites. In this case, the predominant peaks selected are $2\theta = 53.1°$, 49.3°, 47.3°, 36.1°, 32.9°, 32.6°, 31.1°, 30.25°, 28.65°, and 13.15°, and they are averaged. In the above equation, D is the size of a crystallite (in angstrom), $\lambda$ is the wavelength of X-ray used for measurement (in angstrom), $\beta$ is the spread of diffracted rays purely based on the size of crystallites (in radian) (the reference used in an $\alpha$-Al$_2$O$_3$ powder fired at 1,100° C. for 24 hours), K is shape factor (constant, 0.9 in this measurement), and $\theta$ is the Bragg angle of diffracted rays. It is to be noted that $\beta$ is an experimentally determined half-value-width minus the half-value-width of a highly crystalline material measured under the same conditions.

Abrasiveness Measurment

The RDA (Radioactive Dentin Abrasion) value was measured according to the process described in Hefferen, *J. Dent. Res.*, Vol. 55, No. 4, pp. 563–573.

Cleanability Measurement

Tobacco tar was collected in a conventional manner and dissolved in a suitable solvent. The tar solution was uniformly coated onto a tile and dried by heating. The tar-coated tile was placed in a polishing tank and brushed 2,000 times under a load of 200 grams using a suspension of 5 grams of a powder (each calcium hydrogenphosphate sample shown in Tables 1 and 2) in 15 grams of an aqueous solution of 60% glycerin containing 0.3% of sodium carboxymethyl cellulose. At the end of polishing, the tile was visually observed to determine the percent removal of tar therefrom.

The brush used is a commercially available tooth brush having 44 bundles of bristles, a bristle diameter of 8 mils (about 0.2 mm), and a bristle length of 12 mm, made of nylon-62, with the brush hardness designated M (medium) according to the Japanese household product quality indication.

| Evaluation criterion for tar removal | |
|---|---|
| Point | Percentage removal of tobacco tar |
| 1 | 0–10% |
| 2 | 11–20% |
| 3 | 21–30% |
| 4 | 31–40% |
| 5 | 41–50% |
| 6 | 51–60% |
| 7 | 61–70% |
| 8 | 71–80% |
| 9 | 81–90% |
| 10 | 91–100% |

TABLE 1

| | DCP-D (calcium hydrogenphosphate dihydrate) | | |
|---|---|---|---|
| Sample | Average crystallite size (Å) | Average agglomerate diameter* (μm) | |
| No. 1 | — | 9 | Comparison |
| No. 2 | — | 14 | Comparison |

TABLE 2

| Sample | DCP-A (calcium hydrogenphosphate anhydride) | | |
|---|---|---|---|
| | Average crystallite size (Å) | Average agglomerate diameter* (μm) | |
| No. 3 | 4150 | 2** | Comparison |
| No. 4 | 4150 | 16 | " |
| No. 5 | 282 | 13 | " |
| No. 6 | 3810 | 18 | " |
| No. 7 | 375 | 22 | Invention |
| No. 8 | 661 | 10 | " |
| No. 9 | 867 | 7 | " |
| No. 10 | 1660 | 13 | " |
| No. 11 | 2070 | 15 | " |
| No. 12 | 3194 | 10 | " |

*The average agglomerate diameter was measured using a particle size distribution measuring instrument, Microtrac (trade name, available from Leed & Northrup Company).
**obtained by sieving conventional DCP-A and collecting a fraction having an average agglomerate diameter of 2 microns.

TABLE 3

Abrasiveness and cleanability of various calcium hydrogenphosphate samples

| Sample | Mixing ratio | Abrasiveness (RDA value) | Cleanability | |
|---|---|---|---|---|
| DCP-D No. 1 | — | 50 | 2.4 | Comparison |
| DCP-D No. 2 | — | 57 | 2.6 | " |
| DCP-A No. 3 | — | 135 | 4.3 | " |
| DCP-A No. 4 | — | ≧250 | 7.3 | " |
| DCP-D No. 2/ DCP-A No. 4 | 8/2 | 140 | 4.5 | " |
| DCP-D No. 2/ DCP-A No. 4 | 5/5 | 218 | 6.0 | " |
| DCP-A No. 5 | — | 125 | 3.2 | " |
| DCP-A No. 6 | — | ≧250 | 6.8 | " |
| DCP-A No. 7 | — | 118 | 4.9 | Invention |
| DCP-A No. 8 | — | 145 | 6.1 | " |
| DCP-A No. 9 | — | 134 | 5.3 | " |
| DCP-A No. 10 | — | 155 | 6.3 | " |
| DCP-A No. 11 | — | 151 | 6.8 | " |
| DCP-A No. 12 | — | 180 | 7.5 | " |
| DCP-D No. 2/ DCP-A No. 10 | 5/5 | 153 | 6.1 | " |
| DCP-D No. 2/ DCP-A No. 11 | 9/1 | 86 | 4.0 | " |
| DCP-D No. 2/ DCP-A No. 11 | 5/5 | 141 | 6.5 | " |
| DCP-D No. 2/ DCP-A No. 8 | 5/5 | 101 | 5.0 | " |

The abrasiveness (RDA value) of the samples shown in Table 3 is selected relative to the cleanability in FIG. 7. The reference numerals in FIG. 7 corresponds to sample Nos. in Table 3. Those reference numerals within a circle are samples of the present invention.

As seen from the data of Table 3 and FIG. 7, calcium hydrogenphosphate anhydride samples having an average crystallite size of 300 to 3,500 angstroms exhibits a high degree of cleaning action irrespective of low abrasiveness. In the case of calcium hydrogenphosphate dihydrate samples and calcium hydrogenphosphate anhydride samples having an average crystallite size outside the above-defined range, cleanability in proportional to abrasiveness, and thus, abrasiveness must be increased to enhance cleanability.

EXAMPLE 2

The following clinical test was carried out to demonstrate how a dentifrice containing the calcium hydrogenphosphate anhydride abrasive of the invention is effective for making the tooth aesthetically white.

Using three abrasives, A [DCP-D No. 2/DCP-A No. 11 (5/5)], B [DCP-D No. 2/DCP-A No. 4 (8/2)], and C [DCP-D No. 2/DCP-A No. 4 (5/5)], all appearing in Table 3, toothpastes were prepared having the following formulation.

| | |
|---|---|
| Abrasive | 50.0% |
| Propylene glycol | 2.0 |
| Glycerin | 20.0 |
| Sodium saccharin | 0.2 |
| Sodium carboxymethyl cellulose | 0.7 |
| Carrageenan | 0.2 |
| Colloidal silica | 1.0 |
| Sodium lauryl sulfate | 1.5 |
| Flavors | 1.0 |
| Preservatives | trace amount |
| Water | balance |
| | 100.0% by weight |

It is to be noted that in these abrasives, sample DCP-A No. 11 has a specific surface area of 5.1 m²/g and a density of 2.875 g/cm³, sample DCP-A No. 4 has a specific surface are of 1.2 m²/g and a density of 2.890 g/cm³, and sample DCP-D No. 2 has a specific surface area of 1.1 m²/g and a density of 2.32 g/cm³.

A panel consisted of 15 specialized members, and they brushed the tooth over 4 weeks using these toothpastes. The degree of stain on the tooth was evaluated before and after this 4-week brushing according to the following criterion. The results are shown in Table 4.

Teeth Selected For Evaluation

| | |
|---|---|
| Anterior, labial, upper-lower, right-left, Nos. 1-3 | 12 teeth |
| Anterior, lingual, lower, Nos. 1-3 | 6 teeth |
| Total | 18 teeth |

Evaluation Criterion For Tooth Stain

| (I) Area of stains adhered per tooth | |
|---|---|
| Point | Percent area |
| 0 | 0% |
| 1 | 0% < n ≦ 10% |
| 2 | 10% < n ≦ 20% |
| . | . |
| . | . |
| . | . |
| 9 | 80% < n ≦ 90% |
| 10 | 90% < n ≦ 100% |

| (II) Stain density | |
|---|---|
| Point | Color |
| 1 | yellow |
| 2 | brownish yellow |
| 3 | brown |

The original yellow of the tooth itself was neglected in this stain density evaluation.

Using these criteria, the degree of stain on teeth was evaluated in terms of (I) multiplied by (II) for each tooth. It will be readily understood that for each tooth, the worst point is 10×3=30 points. The result for each toothpaste is expressed as an average value per tooth.

TABLE 4

| | Degree of stain | | |
|---|---|---|---|
| Abrasive | Initial | After 4 week brushing | Percent removal |
| A | 1.86 points | 1.55 points | 20.0% |
| B | 1.99 | 1.73 | 13.1 |

TABLE 4-continued

| Abrasive | Degree of stain Initial | After 4 week brushing | Percent removal |
|---|---|---|---|
| C | 2.01 | 1.85 | 8.0 |

As seen from the results of Table 4, the abrasive of the present invention, that is, abrasive A has improved whitening effect irrespective of low abrasiveness.

EXAMPLE 3

Another clinical test was carried out to demonstrate how a dentifrice containing the calcium hydrogenphosphate anhydride abrasive of the invention is effective for making the tooth aesthetically white.

Using abrasives shown in Table 5 having substantially equal abrasiveness in order to avoid that differential abrasion might affect the evaluation of the whitening effect, toothpastes having the following formulation were prepared.

| | |
|---|---|
| Abrasive | 42.0% |
| Propylene glycol | 2.0 |
| Sorbitol | 25.0 |
| Sodium saccharin | 0.1 |
| Sodium carboxymethyl cellulose | 1.1 |
| Colloidal silica | 2.0 |
| Sodium lauryl sulfate | 1.5 |
| Flavors | 1.0 |
| Preservatives | trace amount |
| Water | balance |
| | 100.0% by weight |

TABLE 5

| Abrasive | Average agglomerate diameter | Average crystallite size | Density | Specific surface area | Abrasivity on copper plate |
|---|---|---|---|---|---|
| D: calcium hydrogenphosphate anhydride sample No. 13 | 13.6 μm | 430Å | 2.73 g/cm$^3$ | 17 m$^2$/g | 1.1 mg |
| E: calcium hydrogenphosphate anhydride sample No. 14 | 16.0 μm | 200Å | 2.60 g/cm$^3$ | 28 m$^2$/g | 1.3 mg |
| F: calcium hydrogenphosphate dihydrate sample No. 15 | 15.6 μm | — | — | — | 1.4 mg |

Note: Abrasivity on copper plate was measured in the same manner as in Example 4 shown later.

A number of smokers who had brushed their teeth with an abrasive-free dentifrice for one month and thus had their teeth stained were classified into three panels such that each panel consisted of 14 smokers and the average value of stain was substantially the same among the panels. They brushed for a further three weeks with the toothpaste of the above-mentioned formulation. The stain of teeth was evaluated before and after the tooth stain, five examiners examined the front and rear surfaces of upper two and lower two anteriors in accordance with the following criterion. The stain was expressed as an average point per tooth for each panel member.

| Point | Stain |
|---|---|
| 0 | no stain |
| 1 | the area of stain adhered is less than ⅓ of the total tooth surface |
| 2 | the area of stain adhered is more than ⅓ of the total tooth surface |
| 3 | the area of stain adhered is more than ⅔ of the total tooth surface |

The results are shown in Table 6. The results are expressed as an average value for each panel.

TABLE 6

| Abrasive | Before use | After use | Difference |
|---|---|---|---|
| D | 1.65 | 0.90 | 0.75 |
| E | 1.70 | 1.56 | 0.14 |
| F | 1.68 | 1.55 | 0.13 |

The data of Table 6 prove that the abrasive of the invention, that is, abrasive D has improved whitening effect.

EXAMPLE 4

Calcium hydrogenphosphate samples having different densities and specific surface areas shown in Table 7 were examined for abrasiveness and cleanability by the following procedure in order to establish the correlation between performance and physical properties. The results are also shown in Table 7. The density was obtained by a measurement using a pycnometer followed by calculation as previously described.

Abrasiveness Measurement

Using a suspension of 5 grams of a powder (each calcium hydrogenphosphate sample shown in Table 7) in 15 grams of an aqueous solution of 60% glycerin containing 0.3% of sodium carboxymethyl cellulose, a copper plate having a Vickers hardness of 120 as prescribed in Japanese Industrial Standard H-3361 was brushed 20,000 times for 2 hours under a load of 200 grams in a horizontal abrasion tester. The brush used was the same as used in Example 1. The abrasivity on the copper plate was measured in milligram.

Cleanability Measurement

Cleanability was determined in the same manner as in EXAMPLE 1.

TABLE 7

| Sample* | Average agglomerate diameter (μm) | Mixing ratio by weight | Average crystallite size (Å) | Density (g/cm$^3$) | Specific surface area** (m$^2$/g) | Abrasivity on copper plate (mg) | Cleanability | |
|---|---|---|---|---|---|---|---|---|
| DCP-D No. 1 | 9 | — | — | 2.320 | — | 0.8 | 2.3 | Comparison |
| DCP-D No. 2 | 14 | — | — | 2.320 | — | 1.2 | 2.5 | " |
| DCP-A No. 3 | 2*** | — | 4150 | 2.890 | 4.4 | 17.3 | 4.3 | " |
| DCP-A No. 4 | 16 | — | 4150 | 2.890 | 1.2 | 47.0 | 7.3 | " |

TABLE 7-continued

| Sample* | Average agglomerate diameter (μm) | Mixing ratio by weight | Average crystallite size (Å) | Density (g/cm³) | Specific surface area** (m²/g) | Abrasivity on copper plate (mg) | Clean-ability | |
|---|---|---|---|---|---|---|---|---|
| DCP-D No. 2/DCP-A No. 4 | | 8/2 | — | — | — | 18.5 | 4.5 | " |
| " | | 5/5 | — | — | — | 31.4 | 6.0 | " |
| DCP-A No. 16 | 25 | — | 230 | 2.615 | 28.6 | 1.3 | 2.9 | " |
| DCP-A No. 17 | 15 | — | 830 | 2.706 | 13.2 | 1.5 | 5.6 | Invention |
| DCP-A No. 18 | 10 | — | 1600 | 2.810 | 8.9 | 4.7 | 5.9 | " |
| DCP-A No. 19 | 13 | — | 2850 | 2.861 | 3.0 | 11.3 | 6.6 | " |
| DCP-A No. 20 | 18 | — | 3050 | 2.882 | 2.5 | 20.1 | 6.9 | " |
| DCP-D No. 2/DCP-A No. 19 | | 8/2 | — | — | — | 5.1 | 5.0 | " |
| " | | 5/5 | — | — | — | 10.0 | 6.3 | " |

*DCP-D is calcium hydrogenphosphate dihydrate and DCP-A is calcium hydrogenphosphate anhydride.
**measured by the BET method.
***obtained by sieving conventional DCP-A and collecting a fraction having an average agglomerate diameter of 2 microns.

The abrasivity on copper plate of each sample shown in Table 7 is plotted relative to the cleanability in FIG. 8. The reference numerals in FIG. 8 correspond to the sample Nos. in Table 7. Those reference numerals surrounded by a circle are samples within the scope of the invention.

As seen from the data of Table 7 and FIG. 8, calcium hydrogenphosphate anhydride samples having an average crystallite size of 300 to 3,500 angstroms, a density of 2.650 to 2.885 g/cm³, and a specific surface area of 2.5 to 20 m²/g exhibit abrasiveness and cleanability mutually independently, that is, exhibit increased cleanability irrespective of low abrasiveness, and are comparable in cleaning action to conventional abrasives having an abrasivity of about 20 to 30 mg when they have an abrasivity of about 1 to 5 mg, and to conventional abrasives having an abrasivity of about 30 to 50 mg when they have an abrasivity of about 5 to 20 mg. It was also found that similar effects were achieved by mixtures of calcium hydrogenphosphate anhydride samples having crystallite size, density and specific surface area within the presently defined ranges with calcium hydrogenphosphate dihydrate samples. In the case of calcium hydrogenphosphate anhydride samples having crystallite size, density and specific surface area outside the presently defined ranges, calcium hydrogenphosphate dihydrate samples, and mixtures thereof, cleanability was proportional to abrasiveness, and abrasiveness should be increased in order to enhance cleanability. It was also found that calcium hydrogenphosphate anhydride samples having a density of lower than 2.650 g/cm³ were short of cleaning action.

EXAMPLE 5

A further clinical test was carried out to demonstrate how a dentifrice containing the calcium hydrogenphosphate anhydride abrasive of the invention is effective for making the tooth aesthetically white.

Using abrasives shown in Table 8 having substantially equal abrasiveness in order to avoid that differential abrasion might effect the evaluation of the whitening effect, toothpastes having the same formulation as used in Example 3 were prepared and subjected to the same test as done in Example 3. The results, which are expressed as an average value for each panel, are shown in Table 9.

TABLE 8

| Abrasive | Average agglomerate diameter* (μm) | Average crystallite size (Å) | Density (g/cm³) | Specific surface area (m²/g) | Abrasivity on copper plate (mg) | |
|---|---|---|---|---|---|---|
| G: calcium hydrogenphosphate anhydride No. 18 | 10 | 1600 | 2.810 | 8.9 | 4.7 | Invention |
| H: calcium hydrogenphosphate anhydride No. 16 | 25 | 230 | 2.615 | 28.6 | 1.3 | Comparison |
| I: calcium hydrogenphosphate anhydride No. 3 | 2 | 4150 | 2.890 | 4.4 | 17.3 | " |

*Average agglomerate diameter was measured using a particle size distribution measuring instrument, Microtrac (trade name, available from Leed & Northrup Company).

TABLE 9

| Abrasive | Before use | After use | Difference |
|---|---|---|---|
| G | 1.72 | 0.91 | 0.81 |
| H | 1.72 | 1.53 | 0.19 |
| I | 1.76 | 1.53 | 0.23 |

The data in Table 9 prove that the abrasives of the invention having a density within the range of 2.650 to 2.885 g/cm³ as exemplified by abrasive G have improved whitening effect.

EXAMPLE 6

A variety of calcium hydrogenphosphate samples shown in Table 10 were measured for abrasiveness and cleanability by the same methods as used in Example 1 in order to establish the correlation between physical properties and performance. The results are shown in Table 10.

TABLE 10

Abrading and cleaning properties of various calcium hydrogenphosphate samples

| Sample | Mixing ratio | Abrasion (RDA value) | Clean-ability | |
|---|---|---|---|---|
| DCP-D No. 2 | — | 57 | 2.6 | Comparison |
| DCP-A No. 3 | — | 135 | 4.3 | " |
| DCP-A No. 4 | — | ≧250 | 7.3 | " |
| DCP-D No. 2/ DCP-A No. 4 | 8/2 | 140 | 4.5 | " |
| DCP-D No. 2/ DCP-A No. 4 | 5/5 | 218 | 6.0 | " |
| DCP-A No. 21 | — | 99 | 4.5 | Invention |

TABLE 10-continued

Abrading and cleaning properties of various calcium hydrogenphosphate samples

| Sample | Mixing ratio | Abrasion (RDA value) | Cleanability | |
|---|---|---|---|---|
| DCP-A No. 22 | — | 121 | 5.8 | " |
| DCP-A No. 23 | — | 145 | 7.0 | " |
| DCP-A No. 24 | — | 174 | 6.6 | " |
| DCP-D No. 2/ DCP-A No. 23 | 5/5 | 130 | 6.6 | " |
| DCP-D No. 2/ DCP-A No. 23 | 9/1 | 73 | 4.3 | " |
| DCP-D No. 2/ DCP-A No. 24 | 5/5 | 140 | 6.1 | " |

The calcium hydrogenphosphate samples in Table 10 have physical properties and structure shown in Tables 11–13.

TABLE 11

DCP-D: calcium hydrogenphosphate dihydrate

| Sample No. | Average agglomerate diameter ($\mu$m) | Specific surface area (m$^2$/g) |
|---|---|---|
| 2 | 14 | 1.1 |

TABLE 12

DCP-A: calcium hydrogenphosphate anhydride (prior art)

| Sample No. | Average agglomerate diameter ($\mu$m) | Specific surface area (m$^2$/g) | Density (g/cm$^3$) | Average crystallite size (Å) | Average primary particle size ($\mu$m) |
|---|---|---|---|---|---|
| 3 | 2* | 4.4 | 2.89 | 4150 | 1.5 |
| 4 | 16 | 1.2 | 2.89 | 4150 | about 10 |

*obtained by sieving a prior art DCP-A and collecting a fraction having an average agglomerate diameter of 2 microns.

TABLE 13

DCP-A: calcium hydrogenphosphate anhydride (invention)

| Sample No. | Average agglomerate diameter ($\mu$m) | Specific surface area (m$^2$/g) | Density (g/cm$^3$) | Average crystallite size (Å) | Average primary particle size ($\mu$m) |
|---|---|---|---|---|---|
| 21 | 3.5 | 3.5 | 2.80 | 1630 | 1.2 |
| 22 | 8 | 3.0 | 2.85 | 2510 | 1.0 |
| 23 | 13 | 3.8 | 2.87 | 3040 | 1.2 |
| 24 | 22 | 11.3 | 2.75 | 910 | 0.2 |

It should be noted for the data of Tables 11–13 that the average agglomerate diameter was measured using a particle size distribution measuring instrument, Microtrac (trade name, available from Leed & Northrup Company), the specific surface area was measured by the BET method, and the density was measured using a pycnometer followed by calculation according to the above-described equation. The average crystallite size was measured in the same manner as in Example 1. The primary particle size was obtained on the basis of an electron microphotograph by selecting about 100 representative primary particles relatively facing to the front, measuring the longitudinal and transverse dimensions of each particle, and calculating an arithmetic mean of them.

In FIG. 9, the abrasion (RDA value) is plotted relative to the cleanability of each abrasive. The reference numerals in the figure correspond to the sample Nos. in Table 10. Those reference numerals surrounded by a cirlce are of the present invention.

As seen from the data of Table 10 and FIG. 9, in the case of the prior art calcium hydrogenphosphate dihydrate and calcium hydrogenphosphate anhydride samples, cleanability is proportional to abrasiveness, and abrasiveness must be increased in order to enhance cleanability. Conversely, the calcium hydrogenphosphate anhydride samples of the present invention were found to exhibit enhanced cleanability irrespective of low abrasiveness. It was also found that a mixture of calcium hydrogenphosphate dihydrate and calcium hydrogenphosphate anhydride of the invention had a similar effect.

EXAMPLE 7

Four toothpastes having the following formulations J, K, L and M were prepared, and examined for juice effect and favorableness in the following manner using a sensory panel of 10 members. The results are shown in Tabe 14.

| Formulation J | % by weight |
|---|---|
| Propylene glycol | 2.0 |
| Sodium carboxymethyl cellulose | 1.0 |
| Glycerin | 20.0 |
| Sodium saccharin | 0.2 |
| Colloidal silica | 2.0 |
| Flavors | 1.0 |
| Calcium hydrogenphosphate dihydrate | 24.0 |
| Sodium lauryl sulfate | 1.5 |
| Calcium hydrogenphosphate anhydride No. 25* (present invention) | 24.0 |
| Water | Balance |
| Total | 100.0% |

*average agglomerate diameter 18.3 $\mu$m; specific surface area 3.1 m$^2$/g; density 2.86 g/cm$^3$; average crystallite size 2870 Å; and average primary particle size 1.1 $\mu$m

Formulation K

This is the same as formulation J except that 24.0% of calcium hydrogenphosphate anhydride No. 25 of the present invention is replaced by 24.0% of a prior art calcium hydrogenphosphate anhydride No. 4 (average agglomerate diameter 16.1 $\mu$m; specific surface area 1.2 m$^2$/g, density 2.89 g/cm$^3$; average crystallite size 4150 Å; and average primary particle size about 10 $\mu$m).

Formulation L

This is the same as formulation K except that 0.5% of sodium N-lauroyl sarcosinate is further added. Formulation M This is the same as formulation K except that 1.5% of sodium lauryl sulfate is replaced by 1.5% of α-olefin sulfonate.

Juice Effect Measurement

Ten panel members held one-half cup of noncarbonated, pure orange juice in their mouth some time and then swallowed it down such that they perceived the taste or feel of the juice. Then, they brushed their tooth with the above-prepared toothpaste, and drank the same cup of juice in the same manner as above one minute after the tooth-brushing. A change of taste was evaluated in accordance with the following criterion. The results, which are expressed as a total of the respective points that ten members gave for each toothpaste, are shown in Table 14

Evaluation Criterion

0: no change
−1: taste changed rather worse
−3: taste changed very worse

Favorableness Measurement

Using a panel of 10 members; sensory evaluation was made by Scheffe's pair comparison procedure in accordance with the following criterion.

Evaluation Criterion

As compared with the former toothpaste used in brushing, the latter toothpaste is +2: much favorable.
+2: appreciably favorable.
0: equally favorable.
−1: somewhat unfavorable.
−2: strongly unfavorable.

TABLE 14

| Formulation | Juice effect | Favorableness | |
|---|---|---|---|
| J | −1 | +0.325 | Invention |
| K | −13 | −0.610 | Comparison |
| L | −6 | −0.055 | " |
| M | −2 | +0.340 | " |

The data of Table 14 proves that the toothpaste containing the abrasive of the present invention exhibits improved juice effect and gives a pleasant feel to the mouth. That is, the toothpaste of formulation J having the abrasive of the invention blended therein is significantly improved in juice effect and more favored than that of formulation K having prior art calcium hydrogenphosphate anhydride blended therein and that of formulation L having N-lauroylsarcosinate blended in formulation K, and substantially equivalent in juice effect and favorableness to that of formulation M having α-olefin sulfonate blended therein as a foaming agent.

EXAMPLE 8

A variety of calcium hydrogenphosphate samples having substantially equal average agglomerate diameter were tested for enamel scratchiness by the following method. By the enamel scratchiness used herein is meant the tendency that calcium hydrogenphosphate particles will form scratches in the dental enamel during brushing. The calcium hydrogenphosphate samples used are samples identified as No. 2, No. 4, No. 23, and No. 2/No. 4 (8/2) mixture in Table 10.

Enamel Scratchiness Measurement

A bovine tooth piece cut to a size of 5 mm×5 mm was embedded in a resin, and the bovine tooth enamel was ground to a smooth surface by means of a rotary grinder, and then polished with a No. 1200 emery paper, polished with titanium dioxide grits, and buff polished to a gloss of 100±3.0 as measured by a gloss meter (GLOSS METER VG-10, manufactured by Nihon Denshoku Kogyo K. K.). The gloss of 100 means that the enamel surface is a glossy surface essentially free of defects.

The bovine tooth piece was then mounted in a polishing tank of a horizontal abrasion tester, into which was poured a suspension of 5 grams of a powder (each of calcium hydrogenphosphate samples shown in Table 15) in 15 grams of an aqueous solution of 60% glycerin containing 0.3% of sodium carboxymethyl cellulose. The bovine tooth piece was brushed 2000 strokes for 12 minutes in the tester under a load of 200 grams. The brush used was the same as used in Example 1. At the end of brushing, the gloss of the tooth surface was measured by the gloss meter. The difference between the initial and final gloss values (or gloss reduction) is determined for evaluation of scratchiness. The smaller the gloss reduction, the lower is the scratchiness.

TABLE 15

| Calcium hydrogen-phosphate sample No. in Table 10 | Abrasiveness (RDA value) | Gloss reduction | |
|---|---|---|---|
| DCP-A No. 23 | 145 | −2.1 ± 1.8 | Invention |
| DCP-A No. 4 | ≧250 | −20.5 ± 3.5 | Comparison |
| DCP-D No. 2/ DCP-A No. 4 (8/2) | 140 | −6.4 ± 2.6 | " |
| DCP-D No. 2 | 57 | −0.1 ± 2.9 | " |

As seen from the data of Table 15, the calcium hydrogenphosphate anhydride abrasive of the invention is sufficiently low in scratchiness and causes little damage to the dental enamel. More specifically, the abrasive of the invention identified as DCP-A No. 23 exhibits extremely low scratchiness irrespective of substantially the same abrasiveness as compared with the prior art calcium hydrogenphosphate dihydrate and anhydride samples.

EXAMPLE 9

The abrasiveness and cleanability of various calcium hydrogenphosphate samples were determined by the same methods as in Example 4 to establish the correlation between physical properties and performance. The results are shown in Table 16.

TABLE 16

Abrasivity on copper plate and cleanability of various calcium hydrogenphosphate samples

| Sample | Mixing ratio by weight | Abrasivity (mg) | Cleanability | |
|---|---|---|---|---|
| DCP-D No. 1 | — | 0.8 | 2.3 | Comparison |
| DCP-D No. 2 | — | 1.2 | 2.5 | " |
| DCP-A No. 3 | — | 17.3 | 4.3 | " |
| DCP-A No. 4 | — | 47.0 | 7.3 | " |
| DCP-D No. 2/ DCP-A No. 4 | 8/2 | 18.5 | 4.5 | " |
| DCP-D No. 2/ DCP-A No. 4 | 5/5 | 31.4 | 6.0 | " |
| DCP-A No. 26 | — | 1.2 | 4.4 | Invention |
| DCP-A No. 27 | — | 2.1 | 5.2 | " |

TABLE 16-continued

Abrasivity on copper plate and cleanability of various calcium hydrogenphosphate samples

| Sample | Mixing ratio by weight | Abrasivity (mg) | Cleanability | |
|---|---|---|---|---|
| DCP-A No. 28 | — | 16.4 | 6.3 | " |
| DCP-A No. 29 | — | 19.0 | 5.8 | " |
| DCP-D No. 2/ DCP-A No. 26 | 5/5 | 1.2 | 4.0 | " |
| DCP-D No. 2/ DCP-A No. 28 | 8/2 | 7.1 | 4.9 | " |
| DCP-D No. 2/ DCP-A No. 28 | 5/5 | 14.9 | 6.0 | " |

The calcium hydrogenphosphate samples in Table 16 have average agglomerate diameter, average crystallite size, density, specific surface area, and average roundness shown in Tables 17–19.

TABLE 17

DCP-D: calcium hydrogenphosphate dihydrate

| Sample No. | Average agglomerate diameter (μm) | Specific surface area (m²/g) | Average roundness |
|---|---|---|---|
| 1 | 9 | 1.2 | 0.38 |
| 2 | 14 | 1.1 | 0.36 |

TABLE 18

DCP-A: platy, angular calcium hydrogenphosphate anhydride

| Sample No. | Average agglomerate diameter (μm) | Average crystallite size (Å) | Density (g/cm³) | Specific surface area (m²/g) | Average roundness |
|---|---|---|---|---|---|
| 3 | 2* | 4150 | 2.890 | 4.4 | 0.41 |
| 4 | 16 | 4150 | 2.890 | 1.2 | 0.40 |

*obtained by sieving prior art DCP-A and collecting a fraction having an average agglomerate diameter of 2 microns.

TABLE 19

DCP-A: spherulitic calcium hydrogenphosphate anhydride

| Sample No. | Average agglomerate diameter (μm) | Average crystallite size (Å) | Density (g/cm³) | Specific surface area (m²/g) | Average roundness |
|---|---|---|---|---|---|
| 26 | 17 | 710 | 2.70 | 15.0 | 0.85 |
| 27 | 22 | 1860 | 2.85 | 9.1 | 0.70 |
| 28 | 14 | 2030 | 2.87 | 5.0 | 0.60 |
| 29 | 8 | 2250 | 2.88 | 3.6 | 0.51 |

It should be noted for the data of Tables 17–19 that the average agglomerate diameter was measured using a particle size distribution measuring instrument, Microtrac (trade name, available from Leed & Northrup Company), and the specific surface area was measured by the BET method.

In FIG. 10, the abrasivity on a copper plate brushed with each abrasive is plotted relative to the cleanability of the abrasive. The reference numerals in the figure correspond to the numbers in Table 16. Those reference numerals surrounded by a circle are of the present invention.

As seen from the data of Table 16 and FIG. 10, in the case of the prior art calcium hydrogenphosphate dihydrate and subangular calcium hydrogenphosphate anhydride samples, cleanability is proportional to abrasiveness, and abrasiveness must be increased in order to enhance cleanability. Conversely, the spherulitic calcium hydrogengenphosphate anhydride samples of the present invention were found to exhibit enhanced cleanability independent of abrasiveness, or irrespective of low abrasiveness. The abrasives of the present invention are comparable in cleanability to prior art abrasives having an abrasivity of about 20 to 30 mg when they have an abrasivity of about 1 to 5 mg, and to prior art abrasives having an abrasivity of about 30 to 50 mg when they have an abrasivity of about 5 to 20 mg. It was also found that a mixture of calcium hydrogenphosphate dihydrate and spherulitic calcium hydrogenphosphate anhydride in a weight ratio of 5:5 had a similar effect.

EXAMPLE 10

A variety of calcium hydrogenphosphate samples having substantially equal average agglomerate diameter were determined for abrasiveness and gloss increase. The abrasiveness expressed as an abrasivity on a copper plate was measured in the same manner as in Example 4 while the gloss increase was measured in the following manner. The results are shown in Table 20.

Gloss Increase Measurement

A bovine tooth piece cut to a size of 5 mm×5 mm was embedded in a resin, and the bovine tooth enamel was ground to a smooth surface by means of a rotary grinder, and thereafter polished with a No. 1220 emery paper, polished with calcium hydrogenphosphate anhydride, and then buff polished to a gloss of 80.0±2.0 as measured by a gloss meter (GLOSS METER VG-10, manufactured by Nihon Denshoku Kogyo K.K.).

The thus polished bovine tooth piece was then mounted in a polishing tank of a horizontal abrasion tester, into which was poured a suspension of 5 grams of a powder (each of calcium hydrogenphosphate samples shown in Table 20) in 15 grams of an aqueous solutin of 60% glycerin containing 0.3% of sodium carboxymethyl cellulose. The bovine tooth piece was brushed 7000 strokes for 40 minutes in the tester under a load of 200 grams. The brush used was the same as used in Example 1. At the end of brushing, the gloss of the tooth surface was measured by the gloss meter. The difference between the initial and final gloss values is determined as a gloss increase.

TABLE 20

| Sample | Average agglomerate diameter (μm) | Average roundness | Abrasivity (mg) | Gloss increase | |
|---|---|---|---|---|---|
| DCP-D No. 2 | 14 | 0.36 | 1.2 | +4.0 | Comparison |

TABLE 20-continued

| Sample | Average agglomerate diameter (μm) | Average roundness | Abrasivity (mg) | Gloss increase | |
|---|---|---|---|---|---|
| DCP-A No. 26 | 17 | 0.85 | 1.2 | +11.5 | Invention |

As seen from the data of Table 20, the spherulitic calcium hydrogenphosphate anhydride sample of the present invention can greatly improve the gloss of tooth surface irrespective of substantially the same abrasiveness as compared with the prior art calcium hydrogenphosphate dihydrate.

EXAMPLE 11

Two toothpastes having the following formulation were prepared and examined whether they are favored or not by a sensory panel of 20 memers. The results are shown in Table 21.

| Formulation | % by weight |
|---|---|
| Propylene glycol | 2.5 |
| Sodium carboxymethyl cellulose | 1.2 |
| Glycerin | 25.0 |
| Sodium saccharin | 0.1 |
| Colloidal silica | 2.0 |
| Flavors | 1.0 |
| Sodium lauryl sulfate | 1.5 |
| Magnesium tertiary phosphate octahydrate | 2.0 |
| Abrasive shown in Table 21 | 40.0 |
| Preservative | trace amount |
| Water | balance |
| Total | 100.0% |

TABLE 21

| Abrasive | Mixing ratio | Number of panel members | | | |
|---|---|---|---|---|---|
| | | favorable | Unfavorable | No difference | |
| DCP-D No. 2/ DCP-A No. 4 | 5/5 | 6 | 7 | 7 | Comparison |
| DCP-D No. 2/ DCP-A No. 28 | 5/5 | 13 | 3 | 4 | Invention |

Note:
The tests total to 40 since the order effect is taken into account, that is, one toothpaste is followed by the other in the first test and the other is followed by the one in the second test.

As seen from the data of Table 21, the toothpaste having the spherulitic calcium hydrogenphosphate anhydride abrasive blended therein is more favorable than the toothpaste having the prior art calcium hydrogenphosphate anhydride abrasive blended therein. Fourteen members among 20 panel members reported that the former toothpaste is milder to the mouth. That is, the spherulitic calcium hydrogenphosphate anhydride abrasive of the present invention is improved in oral cavity cleaning action and gives a more pleasant feel to the mouth irrespective of low abrasiveness as compared with the prior art calcium hydrogenphosphate anhydride abrasive.

Examples of toothpastes containing calcium hydrogenphosphate anhydride abrasives according to the present invention are shown below.

All of the toothpastes shown in Examples were prepared by mixing the calcium hydrogenphosphate anhydride abrasive with the other ingredients.

EXAMPLE 12

| Calcium hydrogenphosphate anhydride | 40.0% |
|---|---|
| Propylene glycol | 2.0 |
| Glycerin | 30.0 |
| Sodium carboxymethyl cellulose | 1.3 |
| Colloidal silica | 2.0 |
| Sodium lauryl sulfate | 1.5 |
| Sodium saccharin | 0.2 |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:
| Average agglomerate diameter | 11.0 μm |
|---|---|
| Average crystallite size | 620 Å |
| Density | 2.69 g/cm$^3$ |
| Specific surface area | 15.3 m$^2$/g |
| Average roundness | 0.87 |

EXAMPLE 13

| Calcium hydrogenphosphate anhydride | 16.5% |
|---|---|
| Calcium hydrogenphosphate dihydrate | 23.5 |
| Propylene glycol | 2.0 |
| Glycerin | 10.0 |
| Sorbitol | 10.0% |
| Sodium carboxymethyl cellulose | 0.7 |
| Carrageenan | 0.3 |
| Colloidal silica | 2.0 |
| Sodium lauryl sulfate | 1.5 |
| Sodium saccharin | 0.1 |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:
| Average agglomerate diameter | 22.0 μm |
|---|---|
| Average crystallite size | 380 Å |
| Density | 2.66 g/cm$^3$ |
| Specific surface area | 19.0 m$^2$/g |
| Average roundness | 0.90 |

EXAMPLE 14

| Calcium hydrogenphosphate anhydride | 10.0% |
|---|---|
| Aluminum hydroxide | 30.0 |
| Propylene glycol | 2.0 |
| Sorbitol | 25.0 |
| Sodium carboxymethyl cellulose | 1.2 |
| Colloidal silica | 2.0 |
| Sodium lauryl sulfate | 1.5 |
| Sodium saccharin | 0.1 |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:
| Average agglomerate diameter | 11.0 μm |
|---|---|
| Average crystallite size | 510 Å |
| Density | 2.68 g/cm$^3$ |
| Specific surface area | 15.8 m$^2$/g |
| Average roundness | 0.87 |

EXAMPLE 15

| Calcium hydrogenphosphate anhydride | 35.0% |
|---|---|
| Calcium carbonate | 10.0 |
| Propylene glycol | 2.0 |

-continued

| | |
|---|---|
| Sorbitol | 25.0 |
| Sodium carboxymethyl cellulose | 1.1 |
| Colloidal silica | 2.0 |
| Sodium lauryl sulfate | 1.5 |
| Sodium saccharin | 0.1 |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:
| | | |
|---|---|---|
| Average agglomerate diameter | 7.3 | μm |
| Average crystallite size | 600 | Å |
| Density | 2.73 | g/cm³ |
| Specific surface area | 14.9 | m²/g |
| Average roundness | 0.84 | |

EXAMPLE 16

| | |
|---|---|
| Calcium hydrogenphosphate anhydride | 45% |
| Propylene glycol | 2.0 |
| Sorbitol | 20 |
| Carrageenan | 1.0 |
| Sodium lauryl sulfate | 1.5 |
| Sucrose monopalmitate | 1.0 |
| Sodium saccharin | 0.1 |
| Flavor | 1.0 |
| Dextranase | 2.0 |
| Water | Balance |
| | 100.0% by weight |

*Properties of calcium hydrogenphosphate anhydride:
| | | |
|---|---|---|
| Average agglomerate diameter | 7.3 | μm |
| Average crystallite size | 700 | Å |
| Density | 2.78 | g/cm³ |
| Specific surface area | 13.8 | m²/g |
| Average roundness | 0.80 | |

EXAMPLE 17

| | |
|---|---|
| Calcium hydrogenphosphate anhydride | 40% |
| Calcium hydrogenphosphate dihydride | 10 |
| Glycerin | 15 |
| Sorbitol | 10 |
| Sodium carboxymethyl cellulose | 1.2 |
| Sodium lauryl sulfate | 1.2 |
| Stevioside | 0.1 |
| Flavor | 1.0 |
| Sodium monofluorophosphate | 0.76 |
| Glycyrrhizin | 0.1 |
| Sodium pyrophosphate | 0.05 |
| Water | Balance |
| | 100.0% by weight |

*Properties of calcium hydrogenphosphate anhydride:
| | | |
|---|---|---|
| Average agglomerate diameter | 17.8 | μm |
| Average crystallite size | 500 | Å |
| Density | 2.73 | g/cm³ |
| Specific surface area | 17.6 | m²/g |
| Average roundness | 0.85 | |

EXAMPLE 18

| | |
|---|---|
| Calcium hydrogenphosphate anhydride | 25% |
| Precipitated silica | 8.0 |
| Glycerin | 10 |
| Sorbitol | 35 |
| Carbopol | 0.5 |
| Polyvinyl pyrrolidone | 0.1 |
| Sodium lauryl sulfate | 0.7 |
| Sodium N—lauroylsarcosinate | 0.5 |
| Sodium saccharin | 0.1 |
| Flavor | 1.0 |
| Sodium phosphate | 0.2 |

-continued

| | |
|---|---|
| Tranexamic acid | 0.1 |
| Water | Balance |
| | 100.0% by weight |

*Properties of calcium hydrogenphosphate anhydride:
| | | |
|---|---|---|
| Average agglomerate diameter | 15.1 | μm |
| Average crystallite size | 430 | Å |
| Density | 2.73 | g/cm³ |
| Specific surface area | 17.0 | m²/g |
| Average roundness | 0.75 | |

EXAMPLE 19

| | |
|---|---|
| Calcium hydrogenphosphate anhydride | 30% |
| Aluminum hydroxide | 10 |
| Glycerin | 5% |
| Sorbitol | 20 |
| Polyethelene glycol | 5 |
| Xanthane gum | 1.0 |
| Sodium lauryl sulfate | 1.2 |
| Sodium saccharin | 0.1 |
| Flavor | 1.0 |
| Glycyrrhizin | 0.1 |
| Lauroyl monoglyceride | 0.1 |
| Water | Balance |
| | 100.0% by weight |

*Properties of calcium hydrogenphosphate anhydride:
| | | |
|---|---|---|
| Average agglomerate diameter | 22.1 | μm |
| Average crystallite size | 370 | Å |
| Density | 2.65 | g/cm³ |
| Specific surface area | 19.0 | m²/g |
| Average roundness | 0.75 | |

EXAMPLE 20

| | |
|---|---|
| Calcium hydrogenphosphate anhydride | 16.5% |
| Calcium hydrogenphosphate dihydride | 23.5 |
| Propylene glycol | 2.0 |
| Glycerin | 10.0 |
| sorbitol | 10.0 |
| Sodium carboxymethyl cellulose | 0.7 |
| Carrageenan | 0.3 |
| Colloidal silica | 2.0 |
| Sodium lauryl sulfate | 1.5 |
| Sodium saccharin | 0.1 |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:
| | | |
|---|---|---|
| Average agglomerate diameter | 22.1 | μm |
| Average crystallite size | 1750 | Å |
| Density | 2.84 | g/cm³ |
| Specific surface area | 6.5 | m²/g |
| Average roundness | 0.70 | |

EXAMPLE 21

| | |
|---|---|
| Calcium hydrogenphosphate anhydride | 10.0% |
| Aluminum hydroxide | 30.0 |
| Propylene glycol | 2.0 |
| Sorbitol | 25.0 |
| Sodium carboxymethyl cellulose | 1.2 |
| Colloidal silica | 2.0 |
| Sodium lauryl sulfate | 1.5 |
| Sodium saccharin | 0.1 |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:

-continued

| | |
|---|---|
| Average agglomerate diameter | 11.0 μm |
| Average crystallite size | 1660 Å |
| Density | 2.85 g/cm³ |
| Specific surface area | 5.5 m²/g |
| Average roundness | 0.71 |

EXAMPLE 22

| | |
|---|---|
| Calcium hydrogenphosphate anhydride | 45% |
| Propylene glycol | 2.0 |
| Sorbitol | 20 |
| Carrageenan | 1.0 |
| Sodium lauryl sulfate | 1.5 |
| Sucrose monopalmitate | 1.0 |
| Sodium saccharin | 0.1 |
| Flavor | 1.0 |
| Dextranase | 2.0 |
| Water | Balance |
| | 100.0% by weight |

*Properties of calcium hydrogenphosphate anhydride:

| | |
|---|---|
| Average agglomerate diameter | 8.6 μm |
| Average crystallite size | 2365 Å |
| Density | 2.87 g/cm³ |
| Specific surface area | 3.5 m²/g |
| Average roundness | 0.61 |

EXAMPLE 23

| | |
|---|---|
| Calcium hydrogenphosphate anhydride | 40% |
| Calcium hydrogenphosphate dihydrate | 10 |
| Glycerin | 15 |
| Sorbitol | 10 |
| Sodium carboxymethyl cellulose | 1.2 |
| Sodium lauryl sulfate | 1.2 |
| Stevioside | 0.1 |
| Flavor | 1.0 |
| Sodium monofluorophosphate | 0.76 |
| Glycyrrhizin | 0.1 |
| Sodium pyrophosphate | 0.05 |
| Water | Balance |
| | 100.0% by weight |

*Properties of calcium hydrogenphosphate anhydride:

| | |
|---|---|
| Average agglomerate diameter | 17.8 μm |
| Average crystallite size | 870 Å |
| Density | 2.75 g/cm³ |
| Specific surface area | 10.1 m²/g |
| Average roundness | 0.78 |

EXAMPLE 24

| | |
|---|---|
| Calcium hydrogenphosphate anhydride | 25% |
| Precipitated silica | 8.0 |
| Glycerin | 10 |
| Sorbitol | 35 |
| Carbopol | 0.5 |
| Polyvinyl pyrrolidone | 0.1 |
| Sodium lauryl sulfate | 0.7 |
| Sodium N—lauroylsarcosinate | 0.5 |
| Sodium Saccharin | 0.1 |
| Flavor | 1.0 |
| Sodium phosphate | 0.2 |
| Tranexamic acid | 0.1 |
| Water | Balance |
| | 100.0% by weight |

*Properties of calcium hydrogenphosphate anhydride:

| | |
|---|---|
| Average agglomerate diameter | 15.1 μm |
| Average crystallite size | 3190 Å |
| Density | 2.88 g/cm³ |
| Specific surface area | 2.8 m²/g |
| Average roundness | 0.58 |

EXAMPLE 25

| | |
|---|---|
| Calcium hydrogenphosphate anhydride | 40.0% |
| Propylene glycol | 2.0 |
| Glycerin | 30.0 |
| Sodium carboxymethyl cellulose | 1.3 |
| Colloidal silica | 2.0 |
| Sodium lauryl sulfate | 1.5 |
| Sodium saccharin | 0.2 |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:

| | |
|---|---|
| Average agglomerate diameter | 15.1 μm |
| Average crystallite size | 650 Å |
| Density | 2.70 g/cm³ |
| Specific surface area | 13.0 m²/g |
| Average roundness | 0.81 |

EXAMPLE 26

| | |
|---|---|
| Calcium hydrogenphosphate anhydride | 16.5% |
| Calcium hydrogenphosphate dihydrate | 23.5 |
| Propylene glycol | 2.0 |
| Glycerin | 10.0 |
| Sorbitol | 10.0 |
| Sodium carboxymethyl cellulose | 0.7% |
| Carrageenan | 0.3 |
| Colloidal silica | 2.0 |
| Sodium lauryl sulfate | 1.5 |
| Sodium saccharin | 0.1 |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:

| | |
|---|---|
| Average agglomerate diameter | 11.0 μm |
| Average crystallite size | 1510 Å |
| Density | 2.80 g/cm³ |
| Specific surface area | 8.0 m²/g |
| Average roundness | 0.65 |

EXAMPLE 27

| | |
|---|---|
| Calcium hydrogenphosphate anhydride | 10.0% |
| Aluminum hydroxide | 30.0 |
| Propylene glycol | 2.0 |
| Sorbitol | 25.0 |
| Sodium carboxymethyl cellulose | 1.2 |
| Colloidal silica | 2.0 |
| Sodium lauryl sulfate | 1.5 |
| Sodium saccharin | 0.1% |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:

| | |
|---|---|
| Average agglomerate diameter | 22.1 μm |
| Average crystallite size | 430 Å |
| Density | 2.67 g/cm³ |
| Specific surface area | 18.1 m²/g |
| Average roundness | 0.85 |

EXAMPLE 28

| | |
|---|---|
| Calcium hydrogenphosphate anhydride | 35.0% |
| Calcium carbonate | 10.0 |
| Propylene glycol | 2.0 |

-continued

| | |
|---|---|
| Sorbitol | 25.0 |
| Sodium carboxymethyl cellulose | 1.1 |
| Colloidal silica | 2.0 |
| Sodium lauryl sulfate | 1.5 |
| Sodium saccharin | 0.1 |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:

| | |
|---|---|
| Average agglomerate diameter | 7.3 μm |
| Average crystallite size | 2100 Å |
| Density | 2.83 g/cm$^3$ |
| Specific surface area | 6.1 m$^2$/g |
| Average roundness | 0.68 |

EXAMPLE 29

| | |
|---|---|
| Calcium hydrogenphosphate anhydride | 45% |
| Propylene glycol | 2.0 |
| Sorbitol | 20 |
| Carrageenan | 1.0 |
| Sodium lauryl sulfate | 1.5 |
| Sucrose monopalmitate | 1.0 |
| Sodium saccharin | 0.1 |
| Flavor | 1.0 |
| Dextranase | 2.0 |
| Water | Balance |
| | 100.0% by weight |

*Properties of calcium hydrogenphosphate anhydride:

| | |
|---|---|
| Average agglomerate diameter | 17.8 μm |
| Average crystallite size | 1080 Å |
| Density | 2.75 g/cm$^3$ |
| Specific surface area | 8.9 m$^2$/g |
| Average roundness | 0.73 |

EXAMPLE 30

| | |
|---|---|
| Calcium hydrogenphosphate anhydride | 40% |
| Calcium hydrogenphosphate dihydride | 10 |
| Glycerin | 15 |
| Sorbitol | 10 |
| Sodium carboxymethyl cellulose | 1.2 |
| Sodium lauryl sulfate | 1.2 |
| Stevioside | 0.1 |
| Flavor | 1.0 |
| Sodium monofluorophosphate | 0.76 |
| Glycyrrhizin | 0.1 |
| Sodium pyrophosphate | 0.05 |
| Water | Balance |
| | 100.0% by weight |

*Properties of calcium hydrogenphosphate anhydride:

| | |
|---|---|
| Average agglomerate diameter | 22.1 μm |
| Average crystallite size | 430 Å |
| Density | 2.67 g/cm$^3$ |
| Specific surface area | 18.1 m$^2$/g |
| Average roundness | 0.85 |

EXAMPLE 31

| | |
|---|---|
| Calcium hydrogenphosphate anhydride | 25% |
| Precipitated silica | 8.0 |
| Glycerin | 10 |
| Sorbitol | 35 |
| Carbopol | 0.5% |
| Polyvinyl pyrrolidone | 0.1 |
| Sodium lauryl sulfate | 0.7 |
| sodium N—lauroylsarcosinate | 0.5 |
| Sodium saccharin | 0.1 |
| Flavor | 1.0 |
| Tranexamic acid | 0.1 |
| Sodium phosphate | 0.2 |
| Water | Balance |
| | 100.0% by weight |

*Properties of calcium hydrogenphosphate anhydride:

| | |
|---|---|
| Average agglomerate diameter | 7.3 μm |
| Average crystallite size | 2100 Å |
| Density | 2.83 g/cm$^3$ |
| Specific surface area | 4.3 m$^2$/g |
| Average roundness | 0.68 |

EXAMPLE 32

| | |
|---|---|
| Calcium hydrogenphosphate anhydride | 30% |
| Aluminum hydroxide | 10 |
| Glycerin | 5 |
| Sorbitol | 20 |
| Polyethelene glycol | 5 |
| Xanthane gum | 1.0 |
| Sodium lauryl sulfate | 1.2 |
| Sodium saccharin | 0.1% |
| Flavor | 1.0 |
| Glycyrrhizin | 0.1 |
| Lauroyl monoglyceride | 0.1 |
| Water | Balance |
| | 100.0% by weight |

*Properties of calcium hydrogenphosphate anhydride:

| | |
|---|---|
| Average agglomerate diameter | 11.0 μm |
| Average crystallite size | 1360 Å |
| Density | 2.78 g/cm$^3$ |
| Specific surface area | 8.0 m$^2$/g |
| Average roundness | 0.70 |

EXAMPLE 33

| | |
|---|---|
| Calcium hydrogenphosphate anhydride | 40.0% |
| Propylene glycol | 2.0 |
| Glycerin | 30.0 |
| Sodium carboxymethyl cellulose | 1.3 |
| Colloidal silica | 2.0 |
| Sodium lauryl sulfate | 1.5 |
| Sodium saccharin | 0.2 |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:

| | |
|---|---|
| Average agglomerate diameter | 15.1 μm |
| Average crystallite size | 830 Å |
| Density | 2.70 g/cm$^3$ |
| Specific surface area | 13.2 m$^2$/g |
| Average roundness | 0.80 |

EXAMPLE 34

| | |
|---|---|
| Calcium hydrogenphosphate anhydride | 16.5% |
| Calcium hydrogenphosphate dihydride | 23.5 |
| Propylene glycol | 2.0 |
| Glycerin | 10.0 |
| Sorbitol | 10.0 |
| Sodium carboxymethyl cellulose | 0.7 |
| Carrageenan | 0.3 |
| Colloidal silica | 2.0 |
| Sodium lauryl sulfate | 1.5 |
| Sodium saccharin | 0.1 |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:

| | |
|---|---|
| Average agglomerate diameter | 10.0 μm |

EXAMPLE 35

| | |
|---|---|
| Calcium hydrogenphosphate anhydride | 10.0% |
| Aluminum hydroxide | 30.0 |
| Propylene glycol | 2.0 |
| Sorbitol | 25.0 |
| Sodium carboxymethyl cellulose | 1.2 |
| Colloidal silica | 2.0 |
| Sodium lauryl sulfate | 1.5 |
| Sodium saccharin | 0.1 |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:

| | |
|---|---|
| Average agglomerate diameter | 7.3 μm |
| Average crystallite size | 2100 Å |
| Density | 2.83 g/cm$^3$ |
| Specific surface area | 6.1 m$^2$/g |
| Average roundness | 0.68 |

EXAMPLE 36

| | |
|---|---|
| Calcium hydrogenphosphate anhydride | 35.0% |
| Calcium carbonate | 10.0 |
| Propylene glycol | 2.0 |
| Sorbitol | 25.0 |
| Sodium carboxymethyl cellulose | 1.1 |
| Colloidal silica | 2.0 |
| Sodium lauryl sulfate | 1.5 |
| Sodium saccharin | 0.1 |
| Flavor | 1.0 |
| Sodium monofluorophosphate | 0.76 |
| Preservative | Trace amount |
| Water | Balance |
| | 100.0% by weight |

*Properties of calcium hydrogenphosphate anhydride:

| | |
|---|---|
| Average agglomerate diameter | 20.4 μm |
| Average crystallite size | 330 Å |
| Density | 2.65 g/cm$^3$ |
| Specific surface area | 15.4 m$^2$/g |
| Average roundness | 0.88 |

EXAMPLE 37

| | |
|---|---|
| Calcium hydrogenphosphate anhydride | 45% |
| Propylene glycol | 2.0 |
| Sorbitol | 20 |
| Carrageenan | 1.0 |
| Sodium lauryl sulfate | 1.5 |
| Sucrose monopalmitate | 1.0 |
| Sodium saccharin | 0.1 |
| Flavor | 1.0 |
| Dextranase | 2.0 |
| Water | Balance |
| | 100.0% by weight |

*Properties of calcium hydrogenphosphate anhydride:

| | |
|---|---|
| Average agglomerate diameter | 14.0 μm |
| Average crystallite size | 2850 Å |
| Density | 2.86 g/cm$^3$ |
| Specific surface area | 3.0 m$^2$/g |
| Average roundness | 0.66 |

EXAMPLE 38

| | |
|---|---|
| Calcium hydrogenphosphate anhydride | 40% |
| Calcium hydrogenphosphate dihydride | 10 |
| Glycerin | 15 |
| Sorbitol | 10 |
| Sodium carboxymethyl cellulose | 1.2 |
| Sodium lauryl sulfate | 1.2% |
| Stevioside | 0.1 |
| Flavor | 1.0 |
| Sodium monofluorophosphate | 0.76 |
| Glycyrrhizin | 0.1 |
| Sodium pyrophosphate | 0.05 |
| Water | Balance |
| | 100.0% by weight |

*Properties of calcium hydrogenphosphate anhydride:

| | |
|---|---|
| Average agglomerate diameter | 23.1 μm |
| Average crystallite size | 1080 Å |
| Density | 2.75 g/cm$^3$ |
| Specific surface area | 8.9 m$^2$/g |
| Average roundness | 0.73 |

EXAMPLE 39

| | |
|---|---|
| Calcium hydrogenphosphate anhydride | 25% |
| Precipitated silica | 8.0 |
| Glycerin | 10 |
| Sorbitol | 35 |
| Carbopol | 0.5 |
| Polyvinyl pyrrolidone | 0.1 |
| Sodium lauryl sulfate | 0.7 |
| Sodium N—lauroylsarcosinate | 0.5 |
| Sodium saccharin | 0.1 |
| Flavor | 1.0% |
| Sodium phosphate | 0.2 |
| Tranexamic acid | 0.1 |
| Water | Balance |
| | 100.0% by weight |

*Properties of calcium hydrogenphosphate anhydride:

| | |
|---|---|
| Average agglomerate diameter | 11.5 μm |
| Average crystallite size | 1900 Å |
| Density | 2.87 g/cm$^3$ |
| Specific surface area | 5.3 m$^2$/g |
| Average roundness | 0.60 |

EXAMPLE 40

| | |
|---|---|
| Calcium hydrogenphosphate anhydride | 30% |
| Aluminum hydroxide | 10 |
| Glycerin | 5 |
| Sorbitol | 20 |
| Polyethelene glycol | 5 |
| Xanthane gum | 1.0 |
| Sodium lauryl sulfate | 1.2 |
| Sodium saccharin | 0.1 |
| Flavor | 1.0 |
| Glycyrrhizin | 0.1 |
| Lauroyl monoglyceride | 0.1 |
| Water | Balance |
| | 100.0% by weight |

*Properties of calcium hydrogenphosphate anhydride:

| | |
|---|---|
| Average agglomerate diameter | 11.0 μm |
| Average crystallite size | 1360 Å |
| Density | 2.78 g/cm$^3$ |
| Specific surface area | 8.0 m$^2$/g |
| Average roundness | 0.70 |

EXAMPLE 41

| | |
|---|---|
| Calcium hydrogenphosphate anhydride | 40.0% |
| Propylene glycol | 2.0 |
| Sorbitol | 30.0 |

-continued

| | |
|---|---|
| Average crystallite size | 2930 Å |
| Density | 2.88 g/cm$^3$ |
| Specific surface area | 4.7 m$^2$/g |
| Average roundness | 0.65 |

| -continued | |
|---|---|
| Sodium carboxymethyl cellulose | 1.0 |
| Colloidal silica | 2.0 |
| Sodium lauryl sulfate | 1.5 |
| Sodium saccharin | 0.1 |
| Magnesium tertiary phosphate | 1.0 |
| Flavor | 1.0 |
| Sodium monofluorophosphate | 0.76 |
| Preservative | Trace amount |
| Water | Balance |
| | 100.0% by weight |
| *Properties of calcium hydrogenphosphate anhydride: | |
| Average agglomerate diameter | 18.3 μm |
| Average crystallite size | 2030 Å |
| Density | 2.85 g/cm³ |
| Specific surface area | 5.3 m²/g |
| Average primary particle size | 0.8 μm |

EXAMPLE 42

| | |
|---|---|
| Calcium hydrogenphosphate anhydride | 10.0% |
| Calcium hydrogenphosphate dihydride | 37.0 |
| Propylene glycol | 2.0 |
| Glycerin | 25.0 |
| Sodium carboxymethyl cellulose | 0.8 |
| Carrageenan | 0.3 |
| Colloidal silica | 2.0 |
| Sodium lauryl sulfate | 1.5 |
| Sodium saccharin | 0.1 |
| Magnesium tertiary phosphate | 1.0 |
| Flavor | 1.0 |
| Sodium monofluorophosphate | 0.76 |
| Preservative | Trace amount |
| Water | Balance |
| | 100.0% by weight |
| *Properties of calcium hydrogenphosphate anhydride: | |
| Average agglomerate diameter | 18.3 μm |
| Average crystallite size | 2030 Å |
| Density | 2.85 g/cm³ |
| Specific surface area | 5.3 m²/g |
| Average primary particle size | 0.8 μm |

EXAMPLE 43

| | |
|---|---|
| Calcium hydrogenphosphate anhydride | 21.0% |
| Calcium hydrogenphosphate dihydride | 20.0 |
| Aluminum hydroxide | 5.0 |
| Glycerin | 20.0 |
| Polyethelene glycol | 2.5 |
| Sodium carboxymethyl cellulose | 0.7 |
| Carrageenan | 0.4 |
| Colloidal silica | 2.5 |
| Sodium lauryl sulfate | 1.5 |
| Sodium N—lauroylsarcosinate | 0.5 |
| Sodium saccharin | 0.1 |
| Magnesium tertiary phosphate | 1.0 |
| Flavor | 1.0 |
| Dextranase | 2.0 |
| Preservative | Trace amount |
| Water | Balance |
| | 100.0% by weight |
| *Properties of calcium hydrogenphosphate anhydride: | |
| Average agglomerate diameter | 18.3 μm |
| Average crystallite size | 2030 Å |
| Density | 2.85 g/cm³ |
| Specific surface area | 5.3 m²/g |
| Average primary particle size | 0.8 μm |

EXAMPLE 44

| | |
|---|---|
| Calcium hydrogenphosphate anhydride | 10.0% |
| Aluminum hydroxide | 30.0 |
| Propylene glycol | 2.5 |
| Glycerin | 10.0 |
| Sorbitol | 20.0 |
| Sodium carboxymethyl cellulose | 1.0 |
| Carrageenan | 0.2 |
| Colloidal silica | 3.0 |
| Sodium lauryl sulfate | 1.5 |
| Sodium saccharin | 0.1 |
| Magnesium tertiary phosphate | 1.0 |
| Flavor | 1.0 |
| Sodium monofluorophosphate | 0.76 |
| Preservative | Trace amount |
| Water | Balance |
| | 100.0% by weight |
| *Properties of calcium hydrogenphosphate anhydride: | |
| Average agglomerate diameter | 18.3 μm |
| Average crystallite size | 2030 Å |
| Density | 2.85 g/cm³ |
| Specific surface area | 5.3 m²/g |
| Average primary particle size | 0.8 μm |

EXAMPLE 45

| | |
|---|---|
| Calcium hydrogenphosphate anhydride | 5.0% |
| Calcium hydrogenphosphate dihydride | 40.0 |
| Propylene glycol | 2.0 |
| Glycerin | 15.0 |
| Sorbitol | 20.0 |
| Sodium carboxymethyl cellulose | 1.0 |
| Colloidal silica | 2.0 |
| Sodium lauryl sulfate | 1.0 |
| Sodium N—lauroylsarcosinate | 0.5 |
| Sodium saccharin | 0.1 |
| Flavor | 1.0 |
| Sodium monofluorophosphate | 0.76 |
| Preservative | Trace amount |
| Water | Balance |
| | 100.0% by weight |
| *Properties of calcium hydrogenphosphate anhydride: | |
| Average agglomerate diameter | 18.3 μm |
| Average crystallite size | 2030 Å |
| Density | 2.85 g/cm³ |
| Specific surface area | 5.3 m²/g |
| Average primary particle size | 0.8 μm |

What is claimed is:

1. An abrasive suitable for use in dentifrice compositions consisting of calcium hydrogenphosphate anhydride whose crystallite has an average size of 300 to 3,500 angstroms as measured by X-ray diffractometry.

2. An abrasive suitable for use in dentifrice compositions according to claim 1 wherein the calcium hydrogenphosphate anhydride has a density of 2.650 to 2.885 g/cm³, a specific surface area of 2.5 to 20 m²/g as measured by the BET method, and an average agglomerate diameter of 2 to 30 microns.

3. An abrasive suitable for use in dentifrice compositions according to claim 1 wherein the calcium hydrogenphosphate anhydride is in the form of a cohesive aggregate of plate crystals whose primary particle has an average size of 0.1 to 5 microns.

4. An abrasive suitable for use in dentifrice compositions according to claim 1 wherein the calcium hydrogenphosphate anhydride is spherulitic.

5. An abrasive suitable for use in dentifrice compositions according to claim 4 wherein the spherulitic calcium hydrogenphosphate anhydride has an average roundness of 0.45 to 0.9.

6. An abrasive suitable for use in dentifrice compositions according to claim 2, wherein the calcium hydrogenphosphate anhydride is in the form of a cohesive aggregate of plate cyrstals whose primary particle has an average size of 0.1 to 5 microns.

7. An abrasive suitable for use in dentifrice compositions according to claim 2, wherein the calcium hydrogenphosphate anhydride is spherulitic.

8. An abrasive suitable for use in oral compositions according to claim 1, wherein the calcium hydrogenphosphate anhydride has a density of 2.650 to 2.885 g/cm$^3$.

9. An abrasive suitable for use in oral compositions according to claim 1, wherein the calcium hydrogenphosphate anhydride has a specific surface area of 2.5 to 20 m$^2$/g as measured by the BET method.

10. An abrasive suitable for use in oral compositions according to claim 1, wherein the calcium hydrogenphosphate anhydride has an average agglomerate diameter of 2 to 30 microns.

11. The abrasive of claim 1, which is prepared by reacting phosphoric acid with a suspension of calcium hydroxide and water in the presence of a crystallization modifier capable of controlling the growth of crystals.

12. The abrasive of claim 11, wherein the crystallization modifier is a phosphoric acid condensate.

* * * * *